United States Patent [19]

Yamazaki et al.

[11] Patent Number: 5,163,102
[45] Date of Patent: Nov. 10, 1992

[54] IMAGE RECOGNITION SYSTEM WITH SELECTIVELY VARIABLE BRIGHTNESS AND COLOR CONTROLLED LIGHT SOURCE

[75] Inventors: Masao Yamazaki, Nara; Fumitoshi Yoshimura, Sakurai; Kenzo Nozaki, Ikoma; Junji Ogawa, Yamatokoriyama; Junichi Naemura, Nara, all of Japan

[73] Assignee: Sharp Kabushiki Kaisha, Osaka, Japan

[21] Appl. No.: 671,079

[22] Filed: Mar. 18, 1991

[30] Foreign Application Priority Data

Mar. 19, 1990 [JP] Japan .................................. 2-70958

[51] Int. Cl.$^5$ .............................................. G01J 1/32
[52] U.S. Cl. ................................................ 382/50; 382/8; 250/205
[58] Field of Search ................... 250/205; 235/455; 382/50, 8

[56] References Cited

U.S. PATENT DOCUMENTS

| | | | |
|---|---|---|---|
| 4,694,186 | 9/1987 | Onoda et al. | 250/205 |
| 4,700,061 | 10/1987 | Ishikawa | 282/50 |
| 4,894,524 | 1/1990 | Murase et al. | 250/205 |
| 4,927,266 | 5/1990 | Sugiura et al. | 250/205 |
| 5,029,245 | 7/1991 | Keränen et al. | 250/205 |
| 5,060,065 | 10/1991 | Wasserman | 382/8 |

FOREIGN PATENT DOCUMENTS 62150107 12/1985 Japan .
1-227443 3/1989 Japan .

Primary Examiner—Leo H. Boudreau
Assistant Examiner—Steven P. Klocinski
Attorney, Agent, or Firm—Nixon & Vanderhye

[57] ABSTRACT

An image recognition apparatus includes a light source including a plurality of light emitting diodes having different wavelengths, for illuminating an object, a driver for selectively operating the light emitting diodes and adjusting the brightness thereof, an image pick-up device for photoelectrically transferring the light reflected from the object into an image signal, and an image decision device for comparing a reference image signal with the image signal obtained by the image pick-up device and then deciding whether an image corresponding to the obtained image signal is clearer than an image corresponding to the reference image signal, the image decision device making the driver sequentially operates the light emitting diodes and change the brightness thereof in such a manner that the image corresponding to the image signal is clearer than the image corresponding to the reference image signal.

8 Claims, 5 Drawing Sheets

FIG. 3 (2)
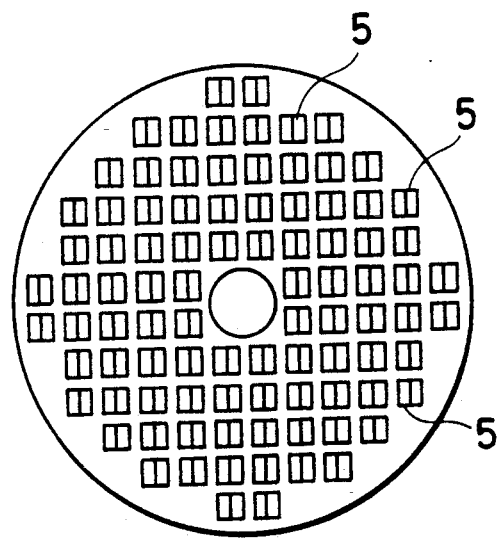

IMAGE RECOGNITION SYSTEM WITH SELECTIVELY VARIABLE BRIGHTNESS AND COLOR CONTROLLED LIGHT SOURCE

BACKGROUND OF THE INVENTION

1. Field of the Invention

The present invention relates to an image recognition apparatus to be used in automatically executing die bonding, wire bonding or the like in semiconductor manufacturing steps so that a position of an electrode of an element can be detected automatically and precisely.

2. Description of the Prior Art

In general, an electrode of a transistor, a diode or the like formed in a semiconductor device, for example, an integrated circuit is rectangular and has sides which are about 100 μm in size. For this reason, in the case where a wire is to be provided on the electrode, image recognition is utilized in order to precisely detect a central portion of the electrode. An image recognition apparatus to be used has a structure in which light is radiated on the electrode as an object from a light source such as a tungsten lamp or a halogen lamp, the light reflected by the electrode is photoelectrically transferred by means of image pick-up means such as a CCD camera or an ITV camera so as to obtain an image signal, the image signal is converted into a binary signal, the binary signal is graphically processed to be compared with an area preset value or a reference pattern, and a central position of a recognition pattern of the electrode as an object to be measured is detected or the quality of the electrode itself is decided (see Japanese Unexamined Patent Publication No. 1-227443).

The material of the electrodes depends on elements formed in an integrated circuit. For example, an electrode such as a transistor is made of aluminum, while an electrode of a light emitting diode or hall element is made of gold. In addition, an oxide film is formed on the surface of the electrode. For this reason, it is required to variably adjust the luminance or luminescent color of the light source so as to be suitable for the material of the electrode or the like in such a manner that a stable image signal can be obtained.

Referring to the lamp which is used as the light source, however, the luminance is not quickly responsive to the change of supply power. Consequently, it takes much time to stabilize the lamp. Since the luminance of the lamp cannot be feed-back controlled at a high speed, it is open-loop controlled by varying a current value supplied to the lamp according to a volume. Consequently, it is impossible to precisely adjust the luminance.

The luminescent color of the lamp can be varied by only a filter. A variety of filters cannot be arranged in a package. It is proposed to use a special light source which is provided with filters corresponding to the electrodes having different materials formed in the integrated circuit. However, the entire apparatus is large-scaled so as not to be put to practical use. Consequently, the luminescent color is not varied correspondingly to the electrode.

Furthermore, the lamp is comparatively large-sized and generates much heat. Consequently, only two or three lamps can be arranged in the package. Therefore, a uniform face emitter cannot be formed, so that a precise image signal cannot be obtained owing to the shadow of the object.

As described above, the brightness of the light source cannot precisely be adjusted, the luminescent color of the light source cannot be varied, and the uniform face emission cannot be carried out. Consequently, the recognition pattern of the electrode is not correct. As a result, the central portion of the extremely small electrode cannot precisely be detected and the quality of the electrode cannot precisely be decided, so that a yield is lowered.

SUMMARY OF THE INVENTION

The present invention provides an image recognition apparatus comprising a light source including a plurality of light emitting diodes having different wavelengths, for illuminating an object, driver means for selectively operating the light emitting diodes and adjusting the brightness thereof, image pick-up means for photoelectrically transferring the light reflected from the object into an image signal, and image decision means for comparing a reference image signal with the image signal obtained by the image pick-up means and then deciding whether an image corresponding to the obtained image signal is clearer than an image corresponding to the reference image signal, the image decision means responsive to an unfavorable comparison causing the driver means to sequentially operate the light emitting diodes so as to change the brightness or the on-off states thereof in such a manner that the image corresponding to the image signal may become clearer than the image corresponding to the reference image signal.

It is preferred that the image decision means makes the driver means initially change the brightness of an energized light emitting diode and then change over to another light emitting diode by energizing the latter and de-energizing the former and so on sequentially in such a manner that permutations of energized/de-energized states of the diodes are exhausted or until the image corresponding to the image signal is clearer than the image corresponding to the reference image signal.

The light source may include a plurality of LED packages, each of the LED packages having a plurality of light emitting diodes built therein.

The image recognition apparatus may further comprise a half mirror for reflecting the light from the light source so as to be led to the object and transmitting the light reflected by the object so as to be led to the image pick-up means.

The image decision means may convert the image signal obtained by the image pick-up means into a binary signal and then decides whether the image corresponding to the image signal is clear depending on the decision whether a difference in high and low levels of the binary signal is greater than a preset reference level.

The light source may have light emitting diodes arranged therein such that the light is focused or may have light emitting diodes arranged such that the light of the diodes is uniformly emitted to provide a surface of light emission.

BRIEF DESCRIPTION OF THE DRAWINGS

FIG. 3 (2) is a bottom view of the light source shown in FIG. 3 (1);

DETAILED DESCRIPTION OF A PREFERRED EMBODIMENT

A preferred embodiment of the present invention will be described in detail with reference to the drawings.

Figure 1:
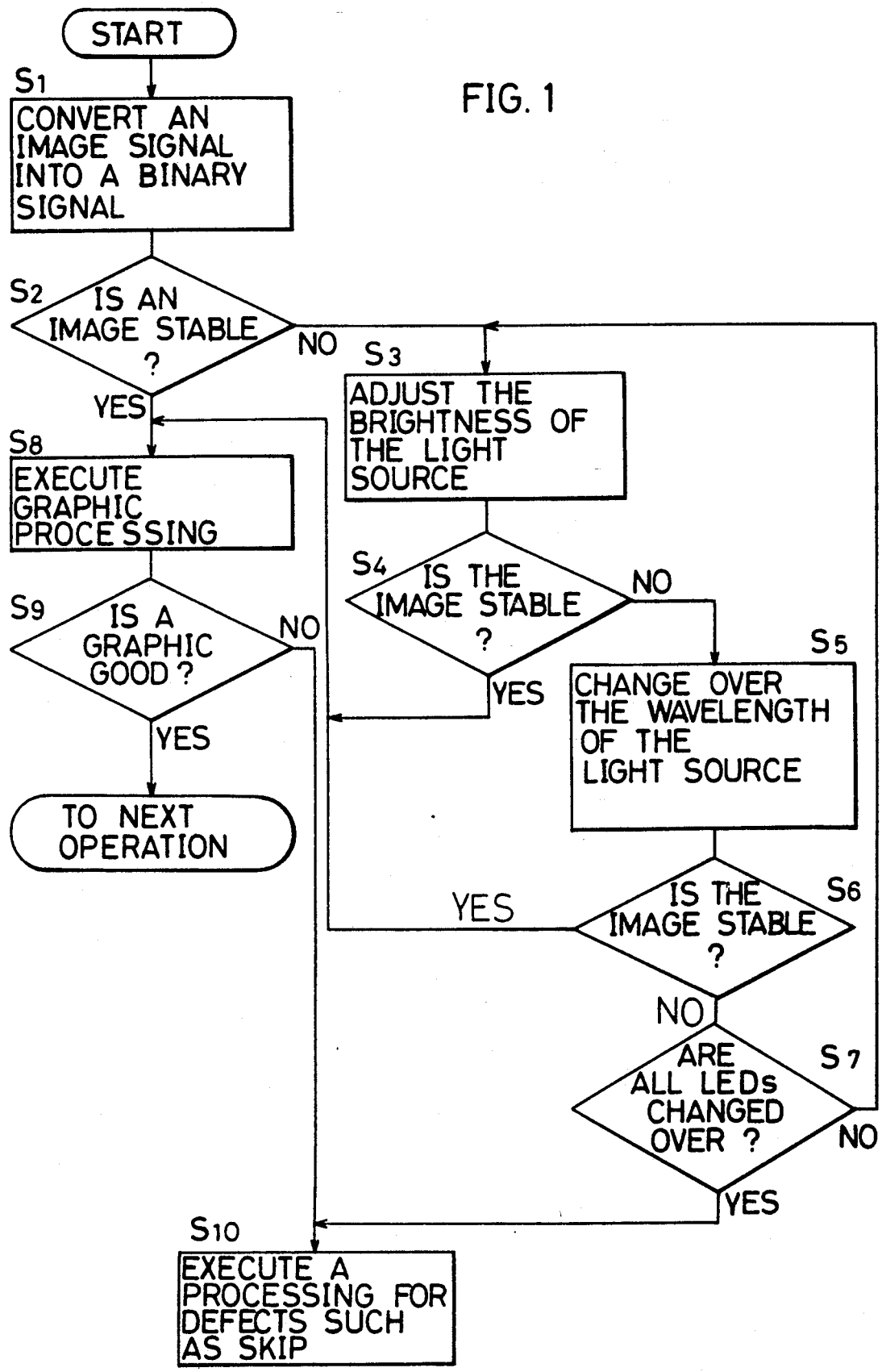
FIG. 1 is a flow chart according to one embodiment of the present invention.
Figure 2:
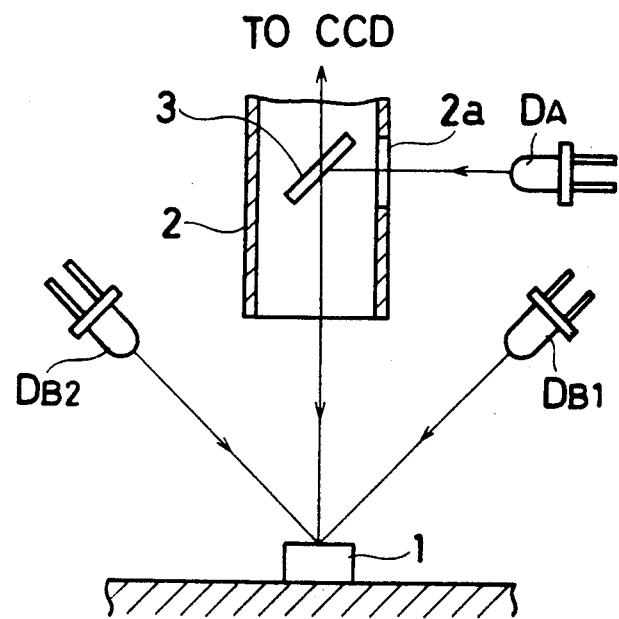
FIG. 2 is an optical view of one example of a light source.

FIG. 1 is a flow chart of image recognition according to one embodiment of the present invention. FIG. 2 is an optical view of a light source to be used for the image recognition in FIG. 1. The light source has a structure in which a plurality of light emitting diodes $D_A$, $D_{B1}$ and $D_{B2}$ having different wavelengths are arranged so that light is focused on an electrode 1 of a semiconductor device as an object. The light emitted from the light emitting diode $D_A$ for coaxial illumination is incident on the inside of a tube 2 through a light incoming hole 2a. In addition, an optical path is changed by a half mirror 3 so that the light is radiated on the electrode 1. The light reflected by the electrode 1 is incident on a CCD solid image pick-up element (not shown) of a CCD camera through the tube 2 so as to be photoelectrically transferred. Consequently, an image signal is obtained.

Figure 4:
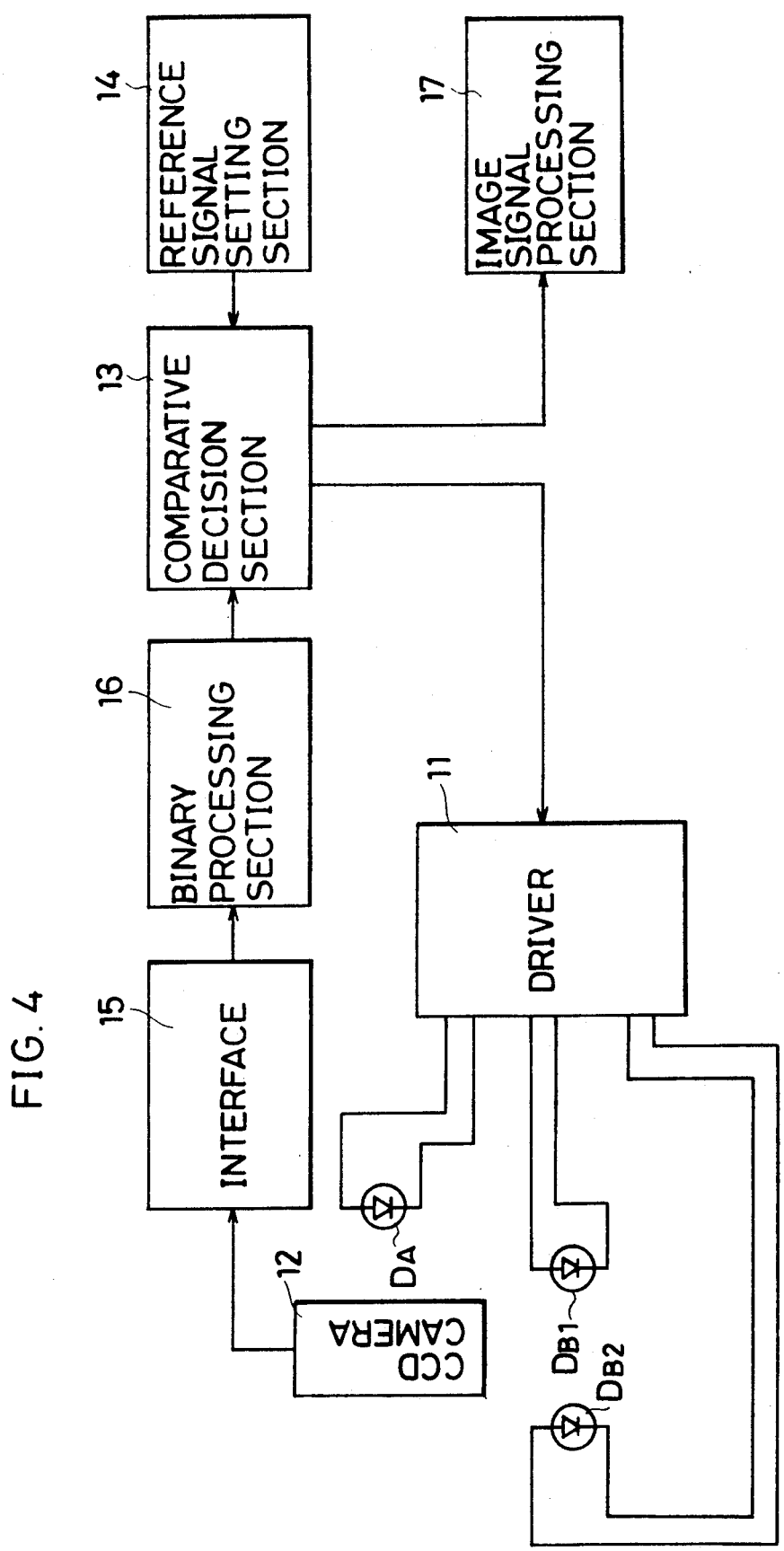
FIG. 4 is a block diagram showing a structure of the embodiment according to the present invention.

FIG. 4 is a block diagram showing a structure of the embodiment according to the present invention. There are shown a plurality of light emitting diodes $D_A$, $D_{B1}$ and $D_{B2}$, a driver 11, a CCD camera 12, a comparative decision section 13, a reference signal setting section 14, an interface 15, a binary processing section 16, and an image signal processing section 17. The light emitting diodes $D_A$, $D_{B1}$ and $D_{B2}$ have different wavelengths for illuminating the object, i.e., the electrode 1. The driver 11 selectively operates the light emitting diodes $D_A$, $D_{B1}$ and $D_{B2}$ and adjusts the brightness thereof. The CCD camera 12 photoelectrically transfers the light reflected by the object so as to obtain an image signal. The comparative decision section 13 compares a reference image signal with the image signal obtained by the CCD camera 12 and decides whether an image corresponding to the obtained image signal is clearer than an image corresponding to the reference image signal (the image is stable). In the case where the image corresponding to the image signal is not clearer than the image corresponding to the reference image signal (the image is not stable), the comparative decision section 13 makes the driver 11 sequentially change over the light emitting diodes $D_A$, $D_{B1}$ and $D_{B2}$ and change the brightness thereof in such a manner that the image corresponding to the image signal is clearer than the image corresponding to the reference image signal.

The reference signal setting section 14 has the reference image signal preset therein.

The comparative decision section 13 makes the driver 11 operate one of the light emitting diodes $D_A$, $D_{B1}$ and $D_{B2}$ to change the brightness thereof and then change over another light emitting diode in such a manner that the image corresponding to the image signal is clearer than the image corresponding to the reference image signal.

More specifically, the image signal obtained from the CCD camera 12 through the interface 15 is converted into binary signals by the binary processing section 16. Then, the comparative decision section 13 using conventional image comparison techniques decides whether the image data corresponding to the image signal is clear (stable) depending on whether a difference in high and low levels of the image binary signals is greater than a reference level preset in the reference signal setting section 14. For example, the numbers of high and low level image dots may be summed to form a ratio for comparison with the preset reference levels.

A feedback control loop is formed by the light emitting diodes $D_A$, $D_{B1}$ and $D_{B2}$, the CCD camera 12, the interface 15, the binary processing section 16, the comparative decision section 13 and the driver 11.

Figure 5:
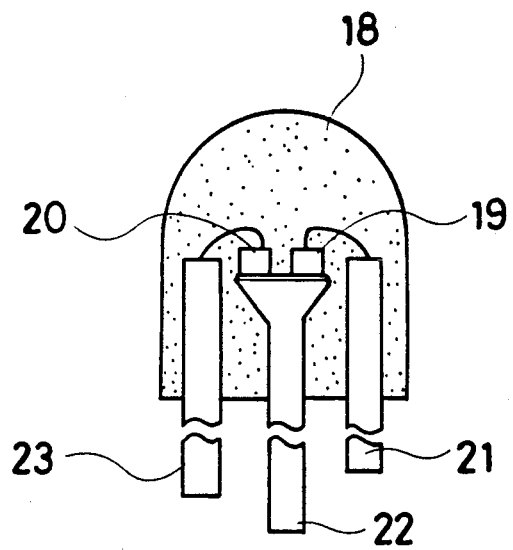
FIG. 5 is a section view of a light emitting diode showing a variant of the present invention.
Figure 6:
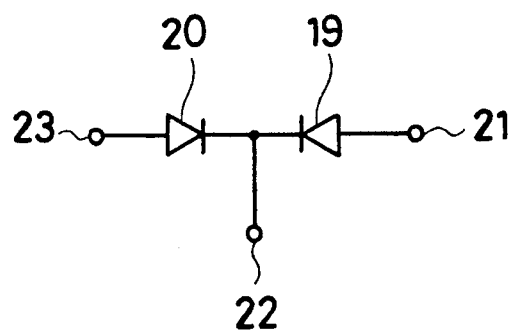
FIG. 6 is an equivalent circuit diagram of the light emitting diode shown in FIG. 5.

The image signal processing section 17 receives the image signal, which can give the clearer image than the image corresponding to the reference image signal, to form the image, and shift the position of the electrode 1 or decide whether the shape of the electrode 1 is good. FIG. 5 is a section view of a light emitting element which can be used in place of each of the light emitting diodes $D_A$, $D_{B1}$ and $D_{B2}$. A translucent resin package 18 has built-in light emitting diodes 19 and 20 of which luminescent colors are different from each other (for example, red and blue) and has lead wires 21 to 23. FIG. 6 is an equivalent circuit diagram of the light emitting element shown in FIG. 5. If the light emitting element is used in place of each of the light emitting diodes $D_A$, $D_{B1}$ and $D_{B2}$, the wavelength of the light for illuminating the object (electrode 1) can be varied in six ways at maximum.

There will be described image recognition by the image signal with reference to FIG. 2. One of the light emitting diodes $D_A$, $D_{B1}$ and $D_{B2}$, for example, the diode $D_A$ is first lighted so that the light is radiated on the electrode 1. The light reflected by the electrode 1 is photoelectrically transferred by the CCD solid image pick-up element of the CCD camera so as to obtain an image signal of the electrode 1. The image signal is converted into a binary signal according to a threshold level (Step S1). The threshold level is set on the basis of a difference in reflectance of the electrode 1 and other parts which is preliminarily and experimentally obtained.

Subsequently, it is decided whether an output level difference in high and low levels of the binary signal is greater than a level which is preset on the basis of a pattern of the electrode 1. Then, it is decided whether the binary signal, i.e., an image for the binary signal is stable (Step S2).

If it is decided that the image is not stable, the brightness of the light emitting diode $D_A$ is variably adjusted (Step S3). Then, it is decided whether the image is stable (Step S4). In the case where a DC power source is used, an amount of supply current is changed so that the brightness of the light emitting diode $D_A$, $D_{B1}$ or $D_{B2}$ can variably be adjusted. In the case where a pulse shape power source is used, a duty ratio is changed so that the brightness of the light emitting diode $D_A$, $D_{B1}$ or $D_{B2}$ can variably be adjusted. In both cases, the luminance is responsive to control signals of the light emitting diodes $D_A$, $D_{B1}$ and $D_{B2}$ very quickly. Consequently, the brightness of the light emitting diode $D_A$, $D_{B1}$ or $D_{B2}$ can be adjusted by feed-back control within a predetermined range of luminance automatically and quickly.

In the case where the image is not stable even if the brightness of the light emitting diode $D_A$ is variably adjusted, another light emitting diode $D_{B1}$ or $D_{B2}$ is changed over so that a luminescent color is varied (Step S5). Then, it is decided whether the image is stable (Step S6). In the case where the image is not stable even if the luminescent color is varied, it is decided whether all the light emitting diodes $D_A$, $D_{B1}$ and $D_{B2}$ are completely lighted (Step S7). If they are not completely lighted, this routine returns to Step S3 in which the brightness of the light emitting diode is variably adjusted again. As far as the image is not stable, the operation of Steps S3 to S7 is repeated so that all the light emitting diodes $D_A$, $D_{B1}$ and $D_{B2}$ are sequentially lighted to vary the luminescent colors. In addition, it is decided whether the image becomes stable while adjusting the brightness of the light emitting diodes $D_A$, $D_{B1}$ and $D_{B2}$.

If it is decided that the image is stable in any of Steps S2, S4 and S6, the image is graphically processed (Step S8). It is decided whether the graphic is a predetermined one, e.g., acceptable (Step S9). The graphic is decided by a feature extraction method or pattern matching method. Referring to the feature extraction method, it is decided whether a graphic area value of the graphically processed electrode is within ±15% of a reference area value which is preset at a binary level. Referring to the pattern matching method, it is decided whether the graphic is good by comparing a recognition pattern of the graphically processed electrode with a preset reference pattern. If it is decided that the graphic is good, this routine proceeds to a next step. In the case where it is decided that the graphic is not good owing to a shift in position of the electrode and the like, or in the case where the image does not become stable even if all the light emitting diodes $D_A$, $D_{B1}$ and $D_{B2}$ are sequentially lighted so that the brightness thereof is variably adjusted, a processing for defects such as skip is executed (Step S10).

As described above, the light emitting diodes $D_A$, $D_{B1}$ and $D_{B2}$ are used as the light sources since they are excellent in responsivity. Consequently, the brightness of the light source can be adjusted by feed-back control automatically and variably. In addition, the light emitting diodes $D_A$, $D_{B1}$ and $D_{B2}$ are small-sized. Therefore, a plurality of light emitting diodes can be provided in a package. Accordingly, a variety of light emitting diodes having different wavelengths are arranged in such a manner that the light is focused. When the light emitting diodes are sequentially changed over, the luminescent color can be varied. Consequently, it is possible to obtain the brightness and most luminescent color suitable for the electrode of the element in the integrated circuit. In addition, the position and quality of the electrode can precisely be detected.

Figure 3:
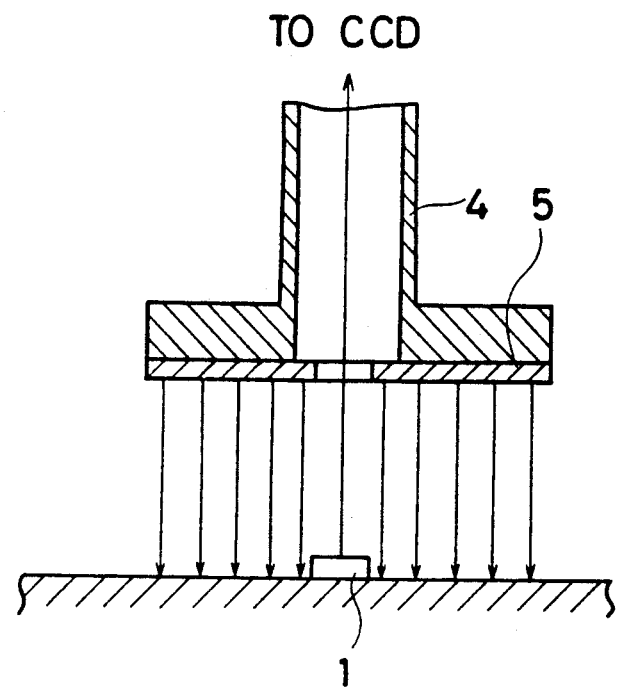
FIG. 3 (1) is an optical view of another example of the light source.

FIGS. 3 (1) and 3 (2) show another example of the light source. A tube 4 has a lot of light emitting diodes 5 provided on the periphery of an opening thereof so that uniform face emission can be obtained. In addition, the shadow of an electrode 1 is removed so that a stable image signal can be obtained. Also in this case, if a light emitting diode with two-color light emitting diodes arranged in a package is employed, a luminescent color can be varied.

According to an image recognition apparatus of the present invention, it is decided whether an image of an object becomes stable while variably adjusting the brightness and luminescent color of a light source. Consequently, the brightness and luminescent color suitable for the object can automatically be set. In addition, image recognition can precisely be executed on a plurality of objects having different reflectances. In particular, in the case where the position and quality of the electrode of the element in the integrated circuit are to be decided, a noticeable effect can be obtained.

What is claimed is:
1. An image recognition apparatus comprising;
 a light source including a plurality of light emitting diodes having different wavelengths, for illuminating an object,
 driver means for selectively operating the light emitting diodes and adjusting the brightness thereof,
 image pick-up means for photoelectrically converting light reflected from the object into an image signal, and
 image decision means for comparing a reference image signal with the image signal obtained by the image pick-up means for determining whether an image corresponding to the obtained image signal is clearer than an image corresponding to the reference image signal,
 the image decision means including means for causing the driver means to sequentially operate the plurality of light emitting diodes so as to change the brightness or the on/off states thereof in such a manner as to selectively vary the brightness and color of the object illuminating light, so that the image corresponding to the obtained image signal becomes clearer than the image corresponding to the reference image signal.

2. An image recognition apparatus according to claim 1, wherein the image decision means causes the driver means to change the brightness of the light emitting diode and then operate another light emitting diode in such a manner that the image corresponding to the image signal is clearer than the image corresponding to the reference image signal.

3. An image recognition apparatus according to claim 1, wherein the light source includes a plurality of LED packages, each of the LED packages having a plurality of light emitting diodes built therein.

4. An image recognition apparatus according to claim 1, further comprising a half mirror for reflecting the light from the light source so as to be led to the object and transmitting the light reflected by the object so as to be led to the image pick-up means.

5. An image recognition apparatus according to claim 1, wherein the image decision means includes means for converting the image signal obtained by the image pick-up means into binary signals and the image decision means determines whether the image corresponding to the obtained image signal is clear depending on a comparison of said binary signals with said reference image signal.

6. An image recognition apparatus according to claim 1, wherein the light source has the light emitting diodes arranged therein such that the light is focused.

7. An image recognition apparatus according to claim 1, wherein the light source has light emitting diodes arranged such that the light of the diodes is uniformly emitted to provide a surface of light emission.

8. An image recognition apparatus according to claim 1, where said plurality of light emitting diodes produce different illuminating colors and said diodes are contained in a package, each said diode being selectively driven by said driver means for illuminating said object with light of variable brightness and color.

* * * * *